(12) United States Patent
Trieu (10) Patent No.: US 8,157,863 B2
(45) Date of Patent: Apr. 17, 2012

(54) DEVICES, APPARATUS, AND METHODS FOR BILATERAL APPROACH TO DISC AUGMENTATION

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 300 days.

(21) Appl. No.: 12/504,108

(22) Filed: Jul. 16, 2009

(65) Prior Publication Data

US 2009/0275913 A1    Nov. 5, 2009

Related U.S. Application Data

(62) Division of application No. 11/412,272, filed on Apr. 27, 2006, now abandoned.

(51) Int. Cl.
*A61F 2/44* (2006.01)
(52) U.S. Cl. ................................. 623/17.12
(58) Field of Classification Search .... 623/17.11–17.16; 606/108; 128/898
See application file for complete search history.

(56) References Cited

U.S. PATENT DOCUMENTS

| | | |
|---|---|---|
| 3,875,595 A | 4/1975 | Froning |
| 4,772,287 A | 9/1988 | Ray et al. |
| 4,863,477 A | 9/1989 | Monson |
| 4,904,260 A | 2/1990 | Ray et al. |
| 5,047,055 A | 9/1991 | Bao et al. |
| 5,146,933 A | 9/1992 | Boyd |
| 5,171,280 A | 12/1992 | Baumgartner |
| 5,192,326 A | 3/1993 | Bao et al. |
| 5,331,975 A | 7/1994 | Bonutti |
| 5,342,298 A | 8/1994 | Michaels et al. |
| 5,344,459 A | 9/1994 | Swartz |
| 5,549,679 A | 8/1996 | Kuslich |
| 5,562,614 A | 10/1996 | O'Donnell |
| 5,562,736 A | 10/1996 | Ray et al. |
| 5,571,189 A | 11/1996 | Kuslich |
| 5,645,597 A | 7/1997 | Krapiva |
| 5,705,780 A | 1/1998 | Bao |
| 5,755,797 A | 5/1998 | Baumgartner |
| 5,824,093 A | 10/1998 | Ray et al. |
| 5,888,220 A | 3/1999 | Felt et al. |
| 5,919,235 A | 7/1999 | Husson et al. |

(Continued)

FOREIGN PATENT DOCUMENTS

WO    WO 2004073563    9/2004

OTHER PUBLICATIONS

Office Action for U.S. Appl. No. 11/412,558, filed Apr. 27, 2006, Jan. 30, 2009, 11 pages.

*Primary Examiner* — Eduardo C Robert
*Assistant Examiner* — Michelle C Eckman (57) ABSTRACT

A method of augmenting a nucleus pulposus of an intervertebral disc comprises forming a first opening in an annulus of the intervertebral disc and forming a second opening in the annulus of the intervertebral disc. The method further comprises providing a space creation instrument including an expandable spacing device and introducing the spacing device through the first opening and into the nucleus pulposus. The method further comprises introducing a material delivery instrument through the second opening and into the nucleus pulposus and expanding the spacing device to create a space within the nucleus pulposus. The method also comprises injecting a biocompatible material from the material delivery instrument and into the space within the nucleus pulposus.

6 Claims, 10 Drawing Sheets

U.S. PATENT DOCUMENTS

| | | | |
|---|---|---|---|
| 5,928,284 | A | 7/1999 | Mehdizadeh |
| 6,022,376 | A | 2/2000 | Assell |
| 6,132,465 | A | 10/2000 | Ray et al. |
| 6,140,452 | A | 10/2000 | Felt et al. |
| 6,165,218 | A | 12/2000 | Husson et al. |
| 6,187,048 | B1 | 2/2001 | Milner et al. |
| 6,231,609 | B1 | 5/2001 | Mehdizadeh |
| 6,248,131 | B1 | 6/2001 | Felt et al. |
| 6,264,695 | B1 | 7/2001 | Stoy |
| 6,375,682 | B1 | 4/2002 | Fleischmann et al. |
| 6,402,750 | B1 | 6/2002 | Atkinson et al. |
| 6,419,704 | B1 | 7/2002 | Ferree |
| 6,482,234 | B1 | 11/2002 | Weber et al. |
| 6,533,817 | B1 | 3/2003 | Norton et al. |
| 6,607,544 | B1 | 8/2003 | Boucher et al. |
| 6,645,248 | B2 | 11/2003 | Casutt |
| 6,692,495 | B1 | 2/2004 | Zacouto |
| 6,692,528 | B2 | 2/2004 | Ward et al. |
| 6,712,853 | B2 | 3/2004 | Kuslich |
| 6,726,721 | B2 | 4/2004 | Stoy et al. |
| 6,733,533 | B1 | 5/2004 | Lozier |
| 6,764,514 | B1 | 7/2004 | Li et al. |
| 6,783,546 | B2 | 8/2004 | Zucherman et al. |
| 6,835,205 | B2 | 12/2004 | Atkinson et al. |
| 6,849,092 | B2 | 2/2005 | Van Dyke et al. |
| 6,893,465 | B2 | 5/2005 | Huang |
| 6,958,077 | B2 | 10/2005 | Suddaby |
| 7,001,431 | B2 | 2/2006 | Bao et al. |
| 2001/0004710 | A1 | 6/2001 | Felt et al. |
| 2001/0049527 | A1 | 12/2001 | Cragg |
| 2002/0016583 | A1 | 2/2002 | Cragg |
| 2002/0026195 | A1 | 2/2002 | Layne et al. |
| 2002/0049498 | A1 | 4/2002 | Yuksel et al. |
| 2002/0059001 | A1 | 5/2002 | Yuksel et al. |
| 2002/0082608 | A1 | 6/2002 | Reiley et al. |
| 2002/0107573 | A1 | 8/2002 | Steinberg |
| 2002/0177866 | A1 | 11/2002 | Weikel et al. |
| 2003/0040800 | A1 | 2/2003 | Li et al. |
| 2003/0074075 | A1 | 4/2003 | Thomas, Jr. et al. |
| 2003/0074076 | A1 | 4/2003 | Ferree et al. |
| 2003/0083642 | A1 | 5/2003 | Boyd et al. |
| 2004/0024463 | A1 | 2/2004 | Thomas, Jr. et al. |
| 2004/0073308 | A1 | 4/2004 | Kuslich et al. |
| 2004/0093087 | A1 | 5/2004 | Ferree et al. |
| 2004/0102774 | A1 | 5/2004 | Trieu |
| 2004/0106999 | A1* | 6/2004 | Mathews .................. 623/17.16 |
| 2004/0133280 | A1 | 7/2004 | Trieu |
| 2004/0186471 | A1* | 9/2004 | Trieu .............................. 606/61 |
| 2004/0186576 | A1 | 9/2004 | Biscup et al. |
| 2004/0210297 | A1 | 10/2004 | Lin et al. |
| 2004/0210315 | A1 | 10/2004 | Li et al. |
| 2004/0215342 | A1 | 10/2004 | Suddaby |
| 2005/0055094 | A1 | 3/2005 | Kuslich |
| 2005/0060036 | A1 | 3/2005 | Schultz et al. |
| 2005/0090901 | A1 | 4/2005 | Studer |
| 2005/0119662 | A1 | 6/2005 | Reiley et al. |
| 2005/0171611 | A1 | 8/2005 | Stoy et al. |
| 2005/0197702 | A1 | 9/2005 | Coppes et al. |
| 2005/0203206 | A1 | 9/2005 | Trieu |
| 2005/0209601 | A1 | 9/2005 | Bowman et al. |
| 2005/0209602 | A1 | 9/2005 | Bowman et al. |
| 2007/0021835 | A1* | 1/2007 | Edidin ....................... 623/17.12 |

* cited by examiner

DEVICES, APPARATUS, AND METHODS FOR BILATERAL APPROACH TO DISC AUGMENTATION

CROSS-REFERENCE TO RELATED APPLICATION

This application is a division of copending U.S. application Ser. No. 11/412,272 filed on Apr. 27, 2006, such copending application being hereby incorporated by reference herein in its entirety.

BACKGROUND

Within the spine, the intervertebral disc functions to stabilize and distribute forces between vertebral bodies. The intervertebral disc comprises a nucleus pulposus which is surrounded and confined by the annulus fibrosis. Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration are frequently treated by replacing or augmenting the existing disc material. Current methods and instrumentation used for treating the disc require a relatively large hole to be cut in the disc annulus to allow introduction of the implant. After the implantation, the large hole in the annulus must be plugged, sewn closed, or other wise blocked to avoid allowing the implant to be expelled from the disc. Besides weakening the annular tissue, creation of the large opening and the subsequent repair adds surgical time and cost. A need exists for devices, instrumentation, and methods for implanting an intervertebral implant using minimally invasive surgical techniques.

SUMMARY

In one embodiment, a method of augmenting a nucleus pulposus of an intervertebral disc comprises forming a first opening in an annulus of the intervertebral disc and forming a second opening in the annulus of the intervertebral disc. The method further comprises providing a space creation instrument including an expandable spacing device and introducing the spacing device through the first opening and into the nucleus pulposus. The method further comprises introducing a material delivery instrument through the second opening and into the nucleus pulposus and expanding the spacing device to create a space within the nucleus pulposus. The method also comprises injecting a biocompatible material from the material delivery instrument and into the space within the nucleus pulposus.

In another embodiment, a system for augmenting a nucleus of an intervertebral disc comprises a first cannula adapted for accessing a nucleus pulposus of the intervertebral disc and a second cannula adapted for accessing the nucleus pulposus of the intervertebral disc. The system further comprises a space creation instrument adapted to be received through the first cannula and including a spacing portion adapted to create a space in the nucleus pulposus of the intervertebral disc. The system further comprises a material delivery instrument adapted to be received through the second cannula and to carry a biocompatible material. The space created in the nucleus pulposus of the intervertebral disc with the space creation instrument is adapted to receive the biomaterial delivered to the space by the material delivery instrument through the second cannula.

In another embodiment, a method for treating a nucleus pulposus of an intervertebral disc comprising creating a first opening to access the intervertebral disc and creating a second opening to access the intervertebral disc. The method further comprises inserting a first space creation instrument having a first spacing device through the first opening and into the nucleus pulposus of the intervertebral disc and inserting a second space creation instrument having a second spacing device through the second opening to access the intervertebral disc. The method further comprises injecting a first biomaterial into the first spacing device to expand the first spacing device and injecting a second biomaterial into the second spacing device to expand the second spacing device. The expansion of the first and second spacing devices occur without removing a portion of the nucleus pulposus.

Additional embodiments are included in the attached drawings and the description provided below.

DETAILED DESCRIPTION

The present disclosure relates generally to devices, methods and apparatus for augmenting an intervertebral disc, and more particularly, to methods and instruments for minimally invasive access procedures. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
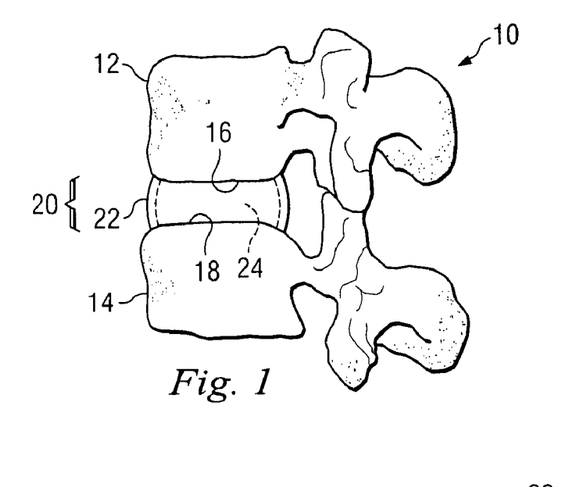
FIG. 1 is a sagittal view of a section of a vertebral column.
Figure 2:
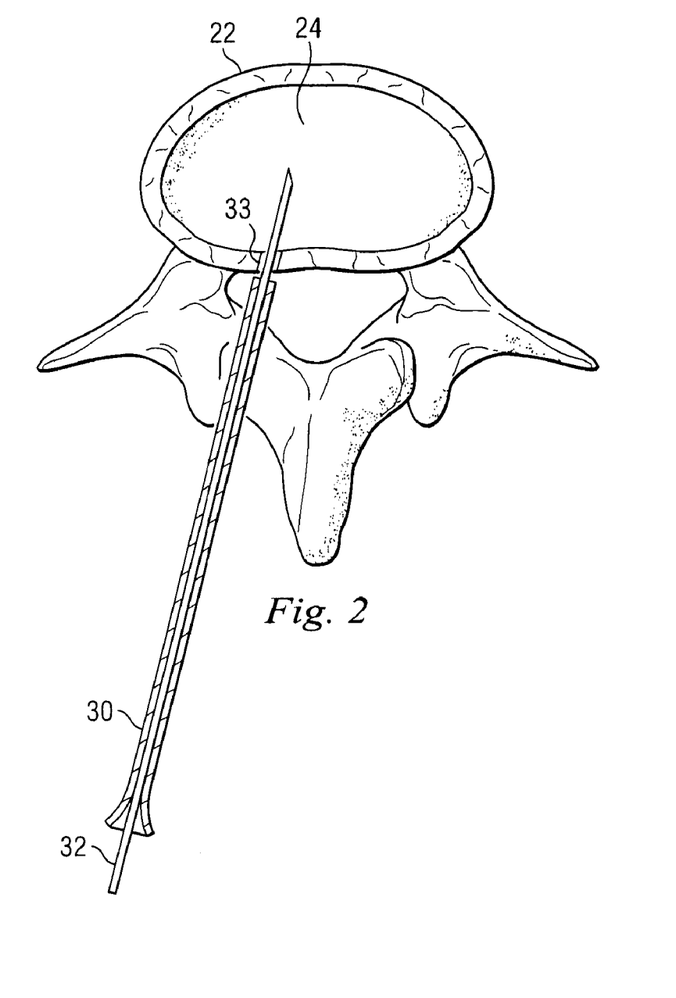
FIGS. 2-5 are a sequence of views of an intervertebral disc treatment including accessing the nucleus, inserting an expandable device, expanding the expandable device to create a space, and filling the space.

Referring first to FIG. 1, the reference numeral 10 refers to a vertebral joint section or a motion segment of a vertebral column. The joint section 10 includes adjacent vertebral bodies 12, 14. The vertebral bodies 12, 14 include endplates 16, 18, respectively. An intervertebral disc space 20 is located between the endplates 16, 18, and an annulus 22 surrounds the space 20. In a healthy joint, the space 20 contains a nucleus pulposus 24.

Referring now to FIGS. 2-5, in this embodiment, the nucleus 24 may be accessed by inserting a cannula 30 into the patient and locating the cannula at or near the annulus 22. An accessing instrument 32, such as a trocar needle or a K-wire is inserted through the cannula 30 and used to penetrate the annulus 22, creating an annular opening 33. This accessing procedure may be repeated at another position on the annulus 22 using a cannula 34 to create an annular opening 35. With the openings 33, 35 created, the accessing instrument 32 may be removed and the cannulae 30, 34 left in place to provide passageway for additional instruments.

In this embodiment, the nucleus is accessed using a posterior bilateral approach. In alternative embodiments, the annulus may be accessed with a lateral approach, an anterior approach, a trans-pedicular/vertebral endplate approach or any other suitable nucleus accessing approach. Although a bilateral approach is described, a unilateral or multi-lateral approach may be suitable. In another alternative embodiment, the nucleus 24 may be accessed through one the of vertebral bodies 12, 14 and through its respective endplate 16, 18. Thus, a suitable bilateral approach to nucleus augmentation may involve a combination approach including an annulus access opening and an endplate access opening.

It is understood that any cannulated instrument including a guide needle or a trocar sleeve may be used to guide the accessing instrument.

In this embodiment, the natural nucleus, or what remains of it after natural disease or degeneration, may remain intact with no tissue removed. In alternative embodiments, partial or complete nucleotomy procedures may be performed.

Figure 3:
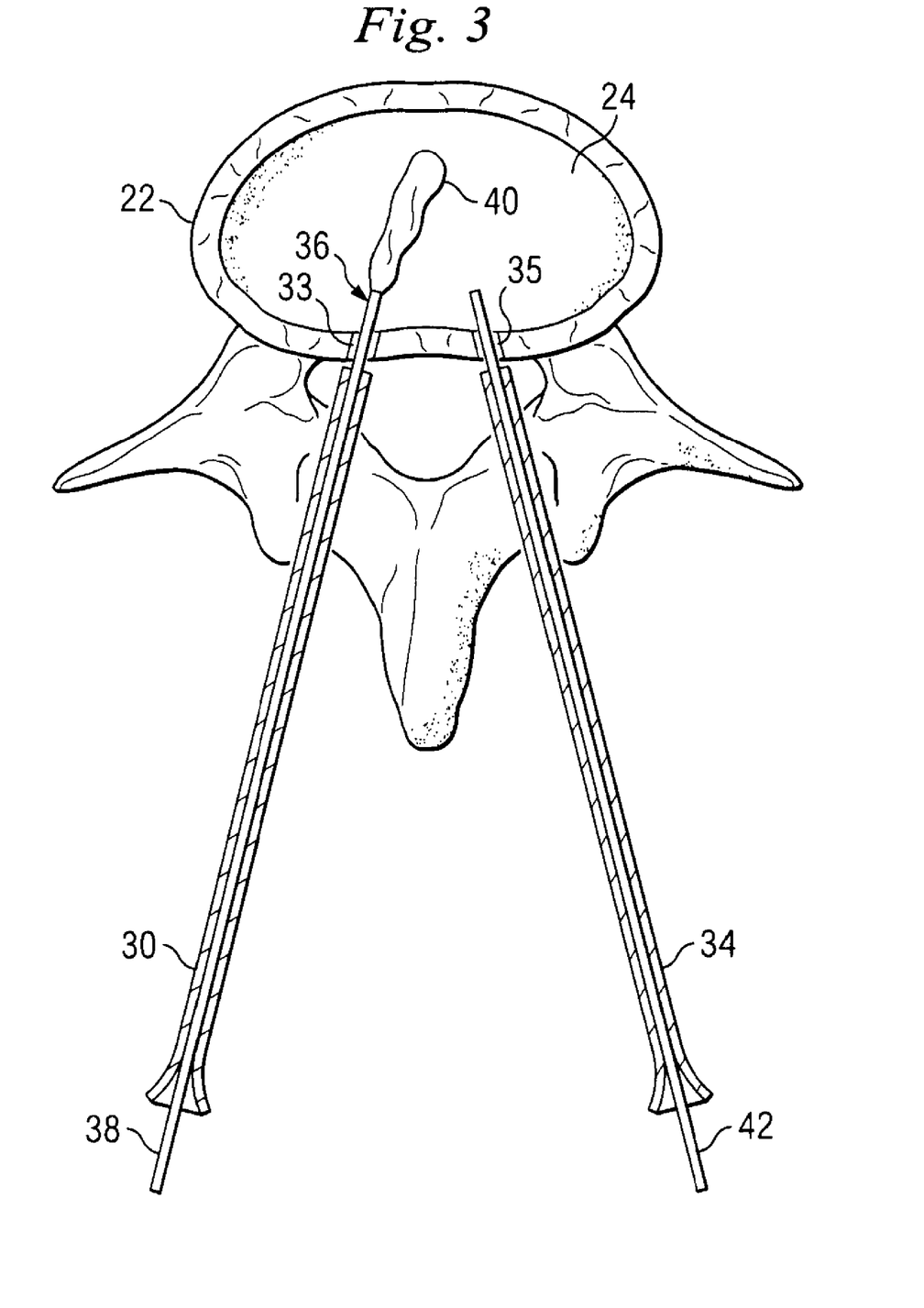

As shown in FIG. 3, a space creating device 36 having a catheter portion 38 and a spacing portion 40 may be inserted through the cannula 30 and the annular opening 33 into the nucleus 24. In this embodiment, the spacing portion 40 is an expandable device such as a balloon which may be formed of elastic or non-elastic materials. The balloon can be of various shapes including conical, spherical, square, long conical, long spherical, long square, tapered, stepped, dog bone, offset, or combinations thereof. Balloons can be made of various polymeric materials such as polyethylene terephthalates, polyolefins, polyurethanes, nylon, polyvinyl chloride, silicone, polyetheretherketone, polylactide, polyglycolide, poly(lactide-co-glycoli-de), poly(dioxanone), poly(.epsilon.-caprolactone), poly(hydroxylbutyrate), poly(hydroxylvalerate), tyrosine-based polycarbonate, polypropylene fumarate or combinations thereof. Additionally, the expandable device may be molded or woven.

In an alternative embodiment, the spacing portion may be mechanical instrument such as a probe or a tamp. A mechanically actuated deformable or expandable instrument which may deform via hinges, springs, shape memory material, etc. may also be used as a spacing portion. In some embodiments, the passage of the spacing portion may be aided with a more rigid guide needle or cannula which will accompany the spacing portion through the cannula and the annulus opening. This guide may be removed after the spacing portion is located within the nucleus 24.

As also shown in FIG. 3, a delivery instrument 42 may be passed through the cannula 34, through the annular opening 35, and into the nucleus 24. The delivery instrument 42 may be an injection needle or other material delivery instrument and may be blunt to avoid puncture or damage to the spacing portion 40.

Figure 4:
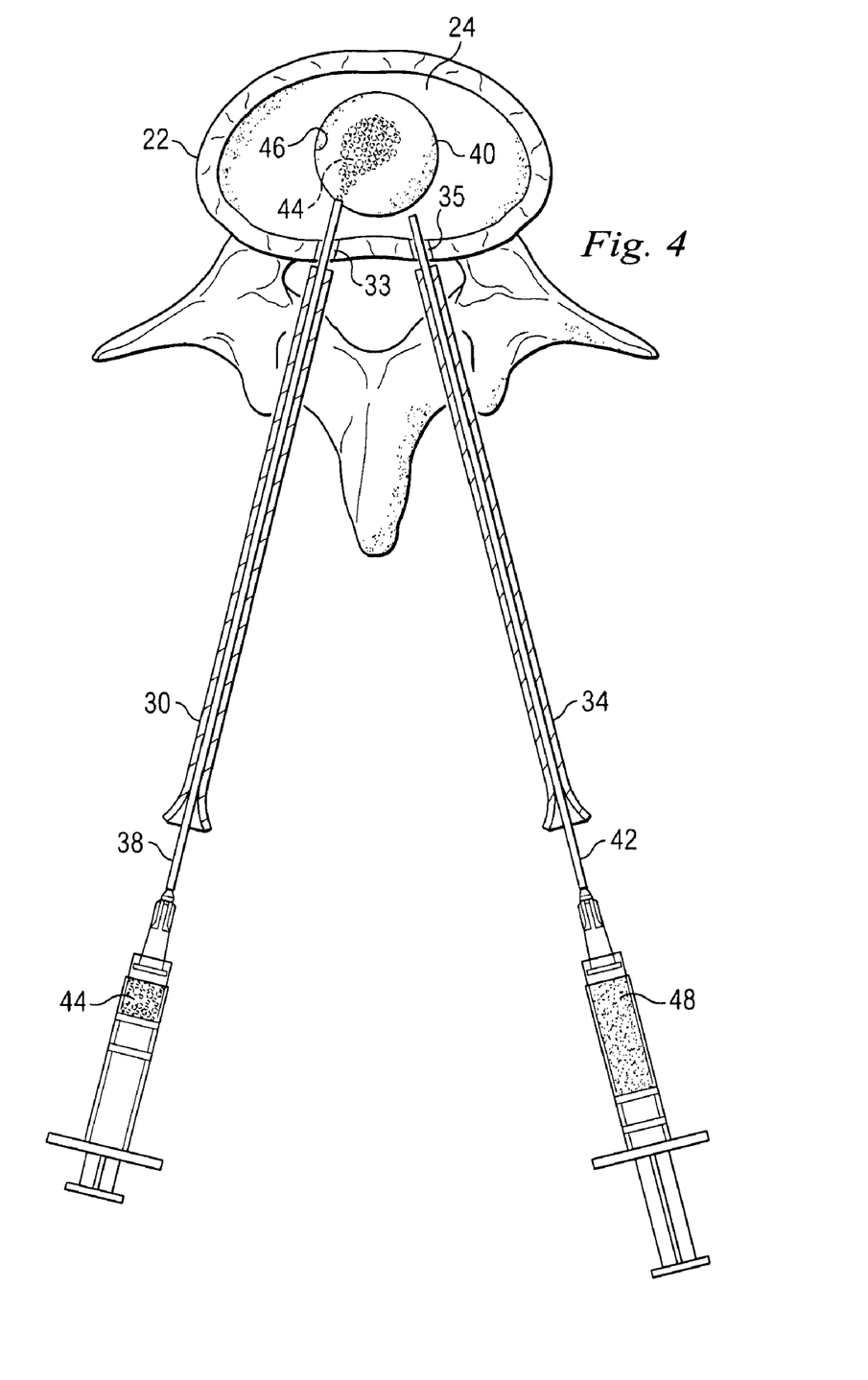

Referring now to FIG. 4, an inflation medium 44 may be pressurized and injected or otherwise passed through the catheter portion 38 of the space creating device 36 to pressurize and inflate the spacing portion 40. The inflation medium 44 may be a saline and/or radiographic contrast medium such as sodium diatrizoate solution sold under the trademark Hypaque® by Amersham Health, a division of GE Healthcare (Amersham, UK). The inflation medium 44 may be injected under pressure supplied by a hand, electric, or other type of powered pressurization device. The internal balloon pressure may be monitored with a well known pressure gauge. The rate of inflation and the pattern, size, or shape of the spacing portion 40 can be varied between patients depending on disc condition. A control device for controlling inflation and dispensing of material is described in further detail in U.S. patent application Ser. No. 11/412,558, entitled "DEVICES, APPARATUS, AND METHODS FOR IMPROVED DISC AUGMENTATION", filed concurrently herewith and incorporated by reference herein in its entirety.

As the spacing portion 40 is gradually inflated, a space 46 is created in the nucleus tissue with the surrounding nucleus tissue becoming displaced or stretched. The inflation may also cause the intradiscal pressure to increase. Both the pressure increase and the direct expansion of the portion 40 may cause the endplates 16, 18 to distract. A pressure gauge and/or a pressure limiter may be used to avoid over inflation or excessive injection.

In an alternative embodiment, the space creating portion may be disposed within the annular opening 33 such that as the space creating portion is expanded, the opening becomes stretched or dilated by the space creating device.

Figure 5:
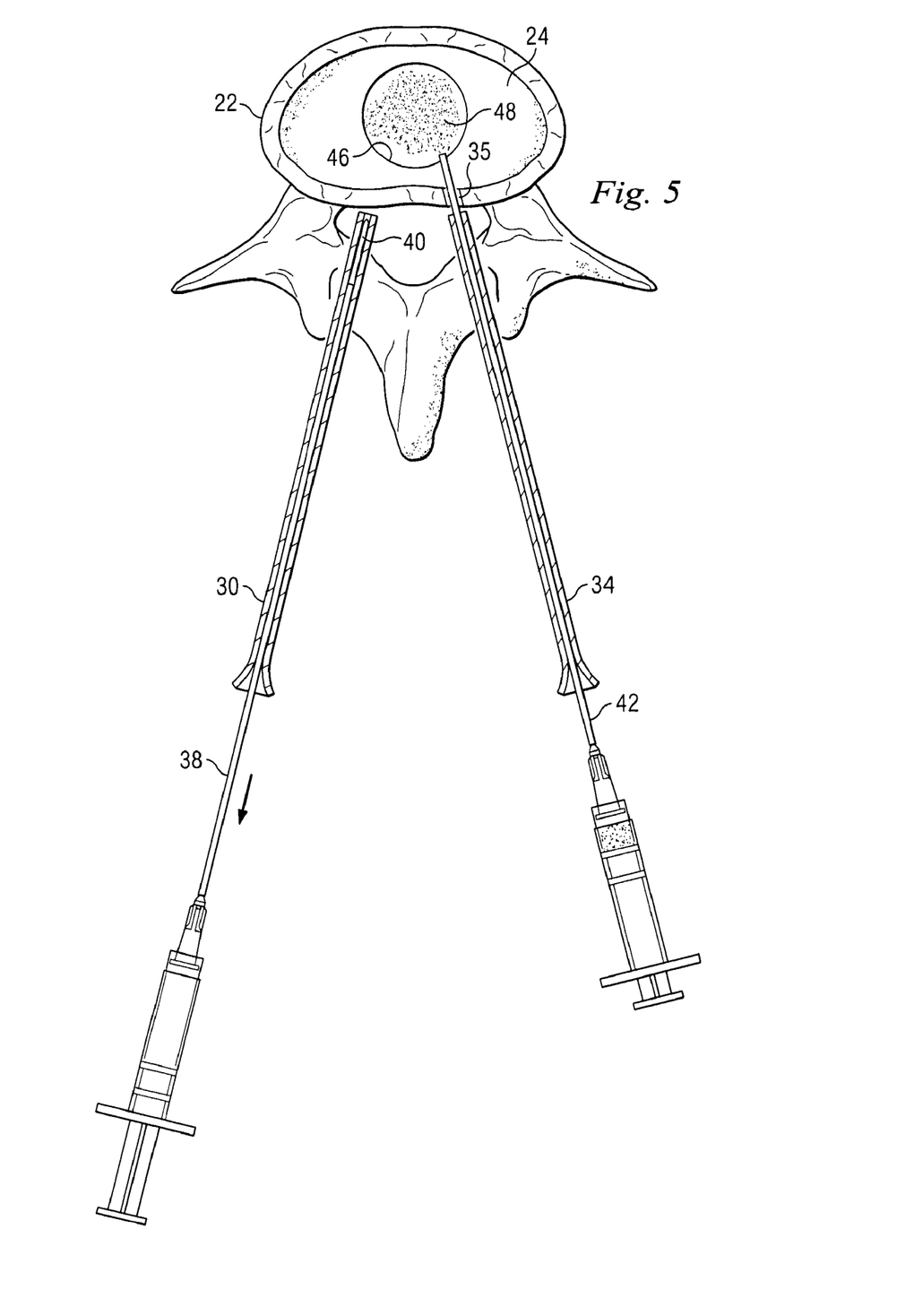

After the space 46 is created, the space creating portion 40 is deflated leaving the space 46 to be filled by a biocompatible material 48 injected from the delivery instrument 42. The injection of the material 48 may be facilitated by using a pressurization device and monitoring gauge. The material 48 may be injected after the space creating portion 40 has been deflated and removed or may be injected while the space creating portion 40 is being deflated and removed. For example, the biomaterial 48 may become increasingly pressurized while the pressure in the space creating portion 40 is lowered. In some procedures, the material 48 may be injected before the space creating portion 40 is removed.

Examples of biocompatible materials 48 which may be used for disc augmentation include natural or synthetic and resorbable or non-resorbable materials. Natural materials include various forms of collagen that are derived from collagen-rich or connective tissues such as an intervertebral disc, fascia, ligament, tendon, skin, or demineralized bone matrix. Material sources include autograft, allograft, xenograft, or human-recombinant origin materials. Natural materials also include various forms of polysaccharides that are derived from animals or vegetation such as hyaluronic acid, chitosan, cellulose, or agar. Other natural materials include other proteins such as fibrin, albumin, silk, elastin and keratin. Synthetic materials include various implantable polymers or hydrogels such as silicone, polyurethane, silicone-polyurethane copolymers, polyolefin, polyester, polyacrylamide, polyacrylic acid, polyvinyl alcohol, polyethylene oxide, polyethylene glycol, polylactide, polyglycolide, poly(lactide-co-glycolide), poly(dioxanone), poly(.epsilon.-caprolactone), poly(hydroxylbutyrate), poly(hydroxylvalerate), tyrosine-based polycarbonate, polypropylene fumarate or combinations thereof. Suitable hydrogels may include poly (vinyl alcohol), poly(acrylic acids), poly(methacrylic acids), copolymers of acrylic acid and methacrylic acid, poly(acrylonitrile-acrylic acid), polyacrylamides, poly(N-vinyl-2-pyrrolidone), polyethylene glycol, polyethyleneoxide, polyacrylates, poly(2-hydroxy ethyl methacrylate), copolymers of acrylates with N-vinyl pyrrolidone, N-vinyl lactams, polyurethanes, polyphosphazenes, poly(oxyethylene)-poly(oxypropylene) block polymers, poly(oxyethylene)-poly(oxypropylene) block polymers of ethylene diamine, poly(vinyl acetate), and sulfonated polymers, polysaccharides, proteins, and combinations thereof.

The selected biocompatible material may be curable or polymerizable in situ. The biocompatible material may transition from a flowable to a non-flowable state shortly after injection. One way to achieve this transition is by adding a crosslinking agent to the biomaterial before, during, or after injection. The biocompatible material in its final state may be load-bearing, partially load-bearing, or simply tissue augmenting with minimal or no load-bearing properties.

Proteoglycans may also be included in the injectable biocompatible material 48 to attract and/or bind water to keep the nucleus 24 hydrated. Regenerating agents may also be incorporated into the biocompatible material. An exemplary regenerating agent includes a growth factor. The growth factor can be generally suited to promote the formation of tissues, especially of the type(s) naturally occurring as components of an intervertebral disc. For example, the growth factor can promote the growth or viability of tissue or cell types occurring in the nucleus pulposus, such as nucleus pulposus cells and chondrocytes, as well as space filling cells, such as fibroblasts and connective tissue cells, such as ligament and tendon cells. Alternatively or in addition, the growth factor can promote the growth or viability of tissue types occurring in the annulus fibrosis, as well as space filling cells, such as fibroblasts and connective tissue cells, such as ligament and tendon cells. An exemplary growth factor can include transforming growth factor-β (TGF-β) or a member of the TGF-β superfamily, fibroblast growth factor (FGF) or a member of the FGF family, platelet derived growth factor (PDGF) or a member of the PDGF family, a member of the hedgehog family of proteins, interleukin, insulin-like growth factor (IGF) or a member of the IGF family, colony stimulating factor (CSF) or a member of the CSF family, growth differentiation factor (GDF), cartilage derived growth factor (CDGF), cartilage derived morphogenic proteins (CDMP), bone morphogenetic protein (BMP), or any combination thereof. In particular, an exemplary growth factor includes transforming growth factor P protein, bone morphogenetic protein, fibroblast growth factor, platelet-derived growth factor, insulin-like growth factor, or any combination thereof.

Therapeutic or biological agents may also be incorporated into the biomaterial. An exemplary therapeutic or biological agent can include a soluble tumor necrosis factor α-receptor, a pegylated soluble tumor necrosis factor α-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, a inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof.

These regenerating, therapeutic, or biological agents may promote healing, repair, regeneration and/or restoration of the disc, and/or facilitate proper disc function. Additives appropriate for use in the claimed invention are known to persons skilled in the art, and may be selected without undue experimentation.

After the biocompatible material 48 is injected, the delivery instrument 42 may be removed from the cannula 34. If the selected biocompatible material 48 is curable in situ, the instrument 42 may be removed during or after curing to minimize leakage. The openings 33, 35 may be small enough, for example less than 3 mm, that they will close or close sufficiently that the injected biocompatible material 48 will remain within the annulus. The use of an annulus closure device such as a suture, a plug, or a material sealant is optional. The cannulae 30, 34 may be removed and the minimally invasive surgical incision closed.

Any of the steps of the method including expansion of the space creating portion 40 and filling the space 46 may be monitored and guided with the aid of imaging methods such as fluoroscopy, x-ray, computed tomography, magnetic resonance imaging, and/or image guided surgical technology such as a Stealth Station™ surgical navigation system (Medtronic, Inc., Minneapolis, Minn.) or a BrainLab system (Heimstetten, Germany).

In an alternative embodiment, the space creating portion may be detachable from the catheter portion and may remain in the nucleus 24 as an implant. In this alternative, the biocompatible material may be injected directly into the space creating portion.

Figure 6:
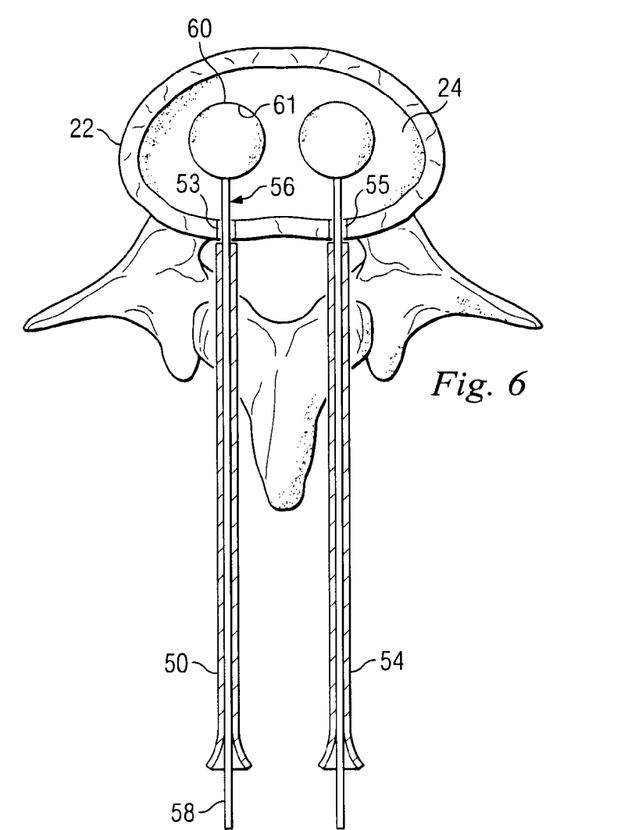
FIGS. 6-7 are sequence views of an intervertebral disc treatment according to another embodiment of the present disclosure.
Figure 7:
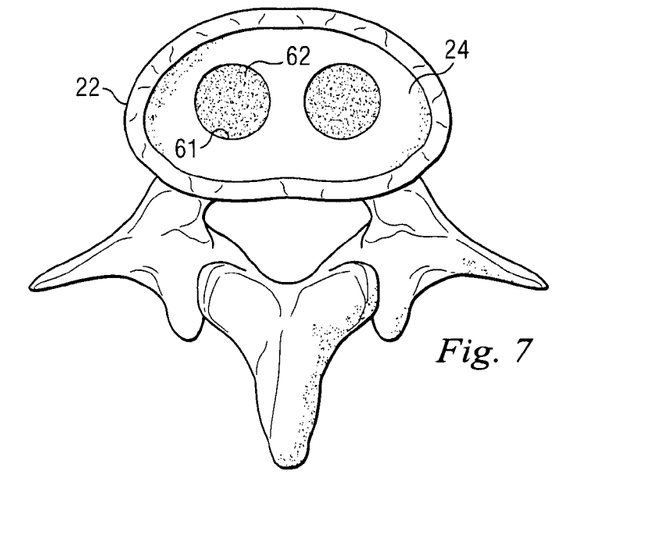

Referring now to FIGS. 6-7, in this embodiment, the nucleus 24 may be accessed by inserting a cannula 50 into the patient and locating the cannula at or near the annulus 22. As described above, an accessing instrument is inserted through the cannula 50 and used to penetrate the annulus 22, creating an annular opening 53. This accessing procedure may be repeated at another position on the annulus 22 using a cannula 54 to create an annular opening 55. With the openings 53, 55 created, the accessing instrument may be removed and the cannulae 50, 54 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 6, a space creating device 56 having a catheter portion 58 and a spacing portion 60 may be inserted through the cannula 50 and the annular opening 53 into the nucleus 24. In this embodiment, the spacing portion is an expandable device such as a balloon which may be formed of elastic or non-elastic materials. The characteristics of the balloon may be the same or similar to those described above. The spacing portion may be inflated and removed as described in further detail in U.S. patent application Ser. No. 10/314,396 ("the '396 application") which is incorporated herein by reference. The space 61 created by the spacing portion may be filled with a biocompatible material 62 using the cannula 54 through the bilateral opening 55 in a manner similar to that described above for FIGS. 2-5 or alternatively, using the same cannula 50 and the opening 53 in a manner similar to that described in the '396 application. The procedure of creating a space in the nucleus 24 may be repeated in another location of the nucleus using the annular opening 55 to pass a space creating device for creating a second space to be filled with a biocompatible material. This procedure may be substantially similar to that described above for creating and filling space 61.

Figure 8:
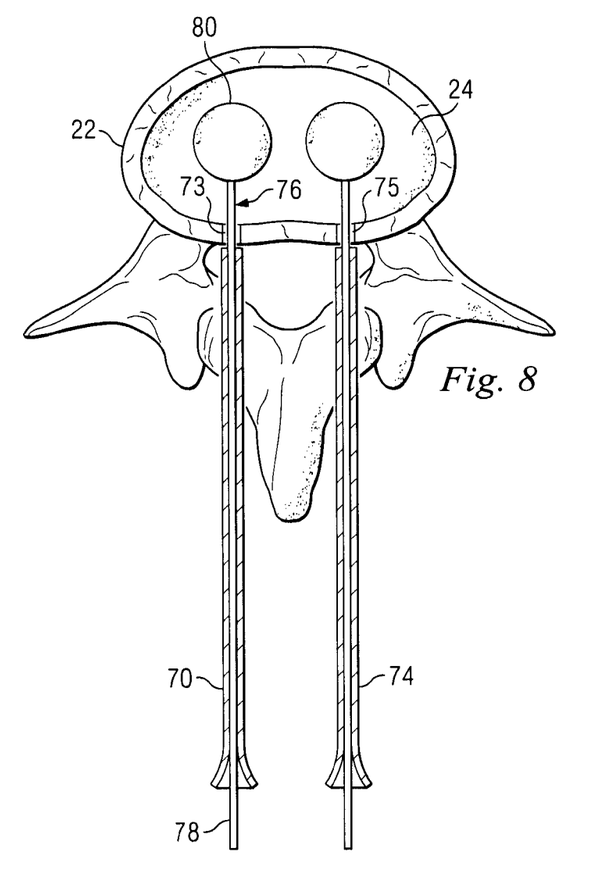
FIGS. 8-9 are sequence views of an intervertebral disc treatment according to another embodiment of the present disclosure.
Figure 9:
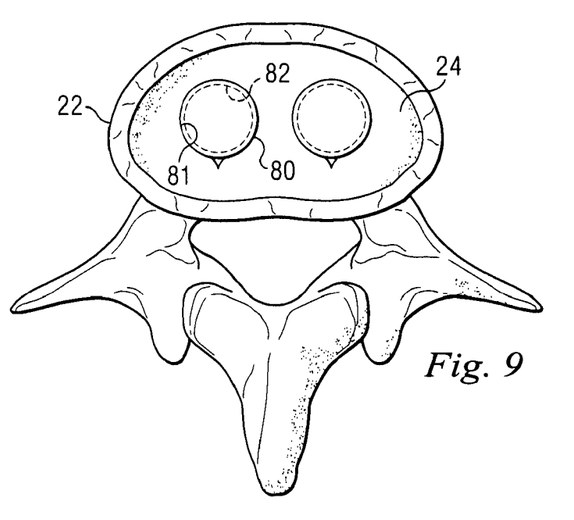

Referring now to FIGS. 8-9, in this embodiment, the nucleus 24 may be accessed by inserting a cannula 70 into the patient and locating the cannula at or near the annulus 22. As described above, an accessing instrument is inserted through the cannula 70 and used to penetrate the annulus 22, creating an annular opening 73. This accessing procedure may be repeated at another position on the annulus 22 using a cannula 74 to create an annular opening 75. With the openings 73, 75 created, the accessing instrument may be removed and the cannulae 70, 74 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 8, a space creating device 76 having a catheter portion 78 and a spacing portion 80 may be inserted through the cannula 70 and the annular opening 73 into the nucleus 24. In this embodiment, the spacing portion is an expandable device such as a balloon which may be formed of elastic or non-elastic materials. The characteristics of the balloon may be the same or similar to those described above. The spacing portion 80 may be pressurized and filled with a biocompatible material 82 as described in further detail in the '396 application. In this embodiment, the filled spacing portion 80 may be detached and left within the nucleus pulposus 24 as an implant. The procedure of creating a space in the nucleus 24 may be repeated in another location of the nucleus using the annular opening 55 to pass a spacing portion for creating a second space, filling the spacing portion with a biocompatible material, and detaching the second spacing portion. This procedure may be substantially similar to the procedure for filling the spacing portion 80. In an alternative embodiment, the spacing portion may be filled with a biocompatible material using the cannula 74 and the bilateral opening 75 in a manner similar to that described above for FIGS. 2-5. This delivery of material through the bilateral opening 75 may occur either before or after the spacing portion is detached from the catheter portion of the space creating device.

Figure 10:
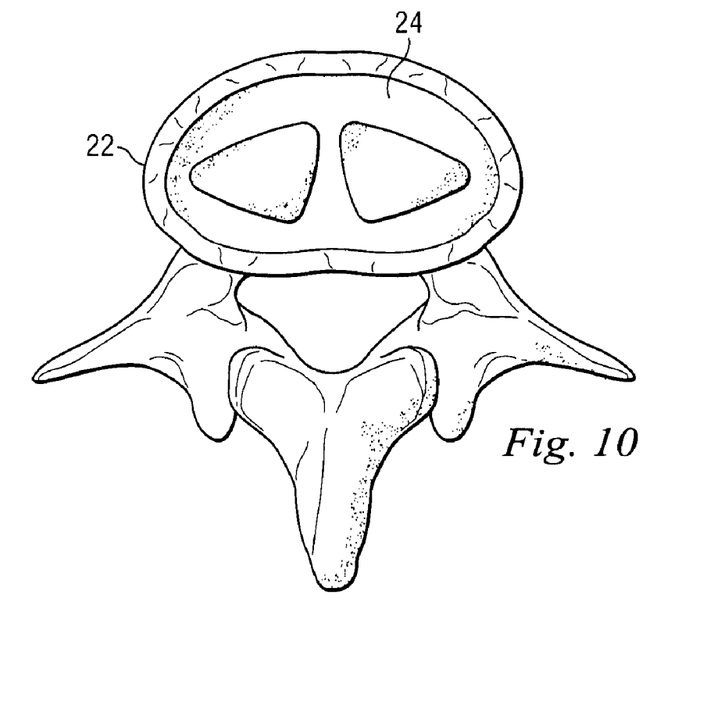
FIGS. 10-11 are alternative intervertebral disc treatments according to other embodiments of the present disclosure.
Figure 11:
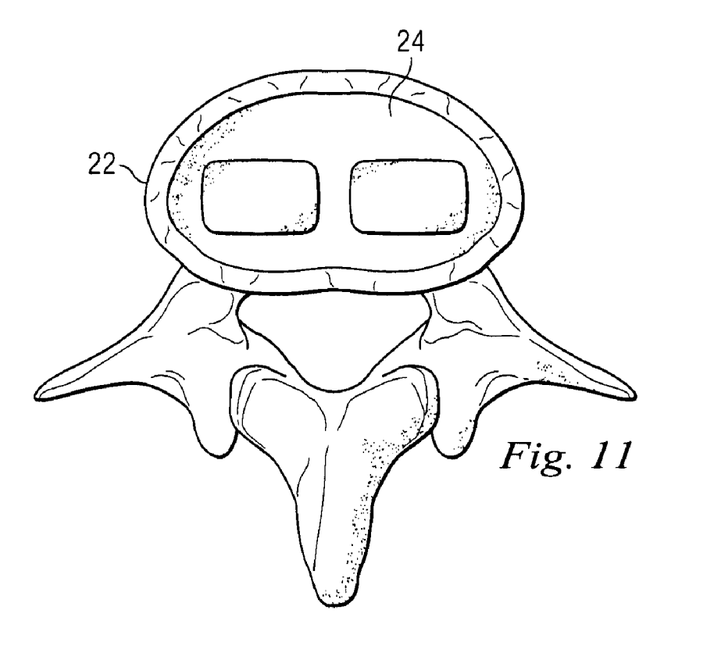

Referring now to FIGS. 10 and 11, spacing portions similar to those described in the previous embodiments may be preformed in various shapes, such as triangular (FIG. 10) or capsular (FIG. 11), to achieve patient-specific goals including compensating for unique nucleus degradation or patient-tailored endplate distraction.

Figure 12:
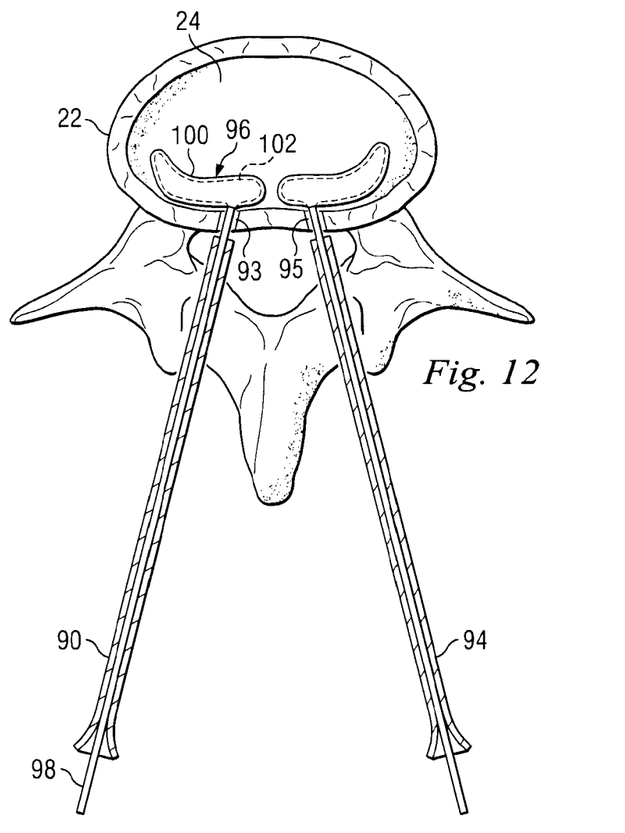
FIGS. 12-13 are sequence views of an intervertebral disc treatment according to another embodiment of the present disclosure.
Figure 13:
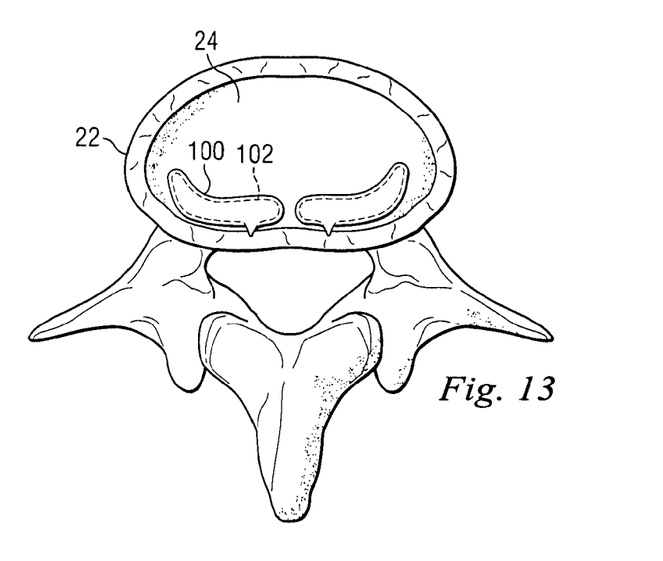

Referring now to FIGS. 12 and 13, in this embodiment, the nucleus 24 may be accessed by inserting a cannula 90 into the patient and locating the cannula at or near the annulus 22. As described above, an accessing instrument is inserted through the cannula 90 and used to penetrate the annulus 22, creating an annular opening 93. This accessing procedure may be repeated at another position on the annulus 22 using a cannula 94 to create an annular opening 95. With the openings 93, 95 created, the accessing instrument may be removed and the cannulae 90, 94 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 12, a space creating device 96 having a catheter portion 98 and a spacing portion 100 may be inserted through the cannula 90 and the annular opening 93 into the nucleus 24. In this embodiment, the spacing portion 100 is an expandable device such as a balloon which may be formed of elastic or non-elastic materials. The characteristics of the balloon may be the same or similar to those described above. The balloon may be shaped to fit along the inner contour of the annulus 22. The spacing portion 100 may be pressurized, filled, and detached as described above. The spacing portion 100 may be filled with a biocompatible material 102 using the cannula 94 and the bilateral opening 95 in a manner similar to that described above for FIGS. 2-5 or using the same cannula 90 and the opening 93 in a manner similar to that described in the '396 application. The procedure of creating a space in the nucleus 24 along the annulus 22 may be repeated in another location of the nucleus using the annular opening 55 to pass a space creating device for creating a second implant to be filled with a biocompatible material. This procedure may be substantially similar to that described above for creating and filling spacing portion 100. The implant created by the filled spacing portion 100 and its bilateral counterpart may be contoured to fit along an interior segment of annulus 22. The resulting implant may support a weakened annulus or reinforce a ruptured annulus to reduce or prevent nucleus herniation. The biocompatible material may be selected to optimize support and flexibility.

Figure 14:
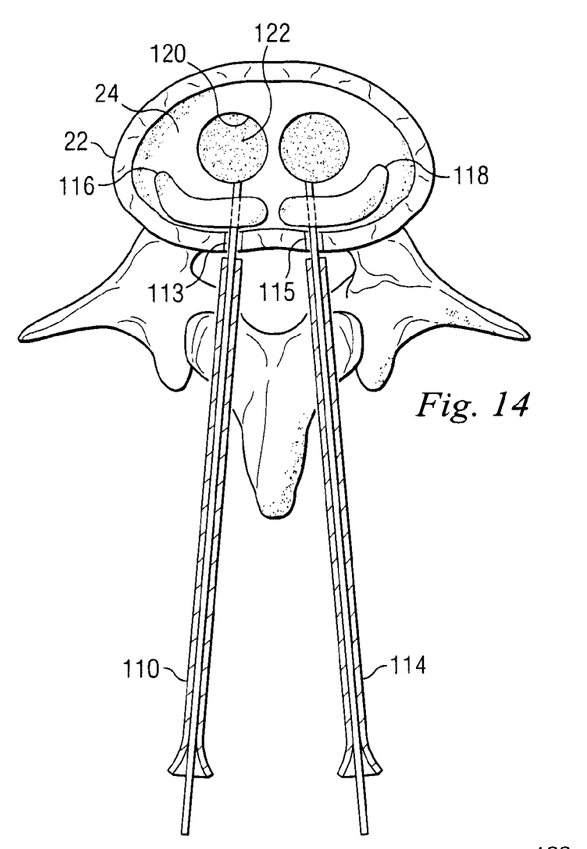
FIGS. 14-15 are sequence views of an intervertebral disc treatment according to another embodiment of the present disclosure.
Figure 15:
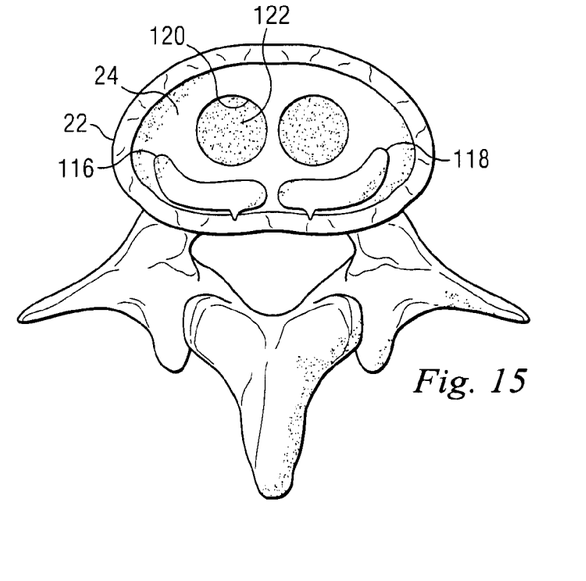

Referring now to FIGS. 14 and 15, in this embodiment, the nucleus 24 may be accessed by inserting a cannula 110 into the patient and locating the cannula at or near the annulus 22. As described above, an accessing instrument is inserted through the cannula 110 and used to penetrate the annulus 22, creating an annular opening 113. This accessing procedure may be repeated at another position on the annulus 22 using a cannula 114 to create an annular opening 115. With the openings 113, 115 created, the accessing instrument may be removed and the cannulae 110, 114 left in place to provide bilateral passageways for additional instruments. In this embodiment, the natural nucleus, or what remains of it after natural disease or degeneration, may remain intact with no tissue removed. In alternative embodiments, partial or complete nucleotomy procedures may be performed.

As shown in FIG. 14, annulus contoured spacing portions 116, 118 may be inserted, detached, and filled as described above in FIG. 12. The resulting implant may support a weakened annulus or reinforce a ruptured annulus to reduce or prevent nucleus herniation. The biocompatible filling material may be selected to optimize support and flexibility. These annulus reinforcing spacing portions 116, 118 may be used in conjunction with the more centralized nucleus spacing procedures described in FIGS. 2-11. In this embodiment, an additional spacing portion may be inserted through the filled spacing portions 116, 118 and expanded within the nucleus 24 to create a space 120. The space 120 may be filled with a biomaterial 122. More spacing portions may be inserted to create additional filled spaces in the nucleus 24. The use of annular spacing portions in conjunction with more centralized spacing portions may help to prevent the more centralized biomaterial and the natural nucleus tissue from migrating through annular defects or openings. The biomaterials selected for filling the various spaces and spacing portions may be the same or different depending upon the desired result.

In an alternative embodiment, a delivery instrument may be inserted through the spacing portions 116, 118 to deposit a biocompatible material directly into the nucleus 24 without creating an additional space within the nucleus. In this embodiment, the spacing portions serve to block migration or expulsion of the biocompatible material through the annulus, however the material may be more dispersed within the nucleus rather than concentrated in a pre-formed space.

Figure 16:
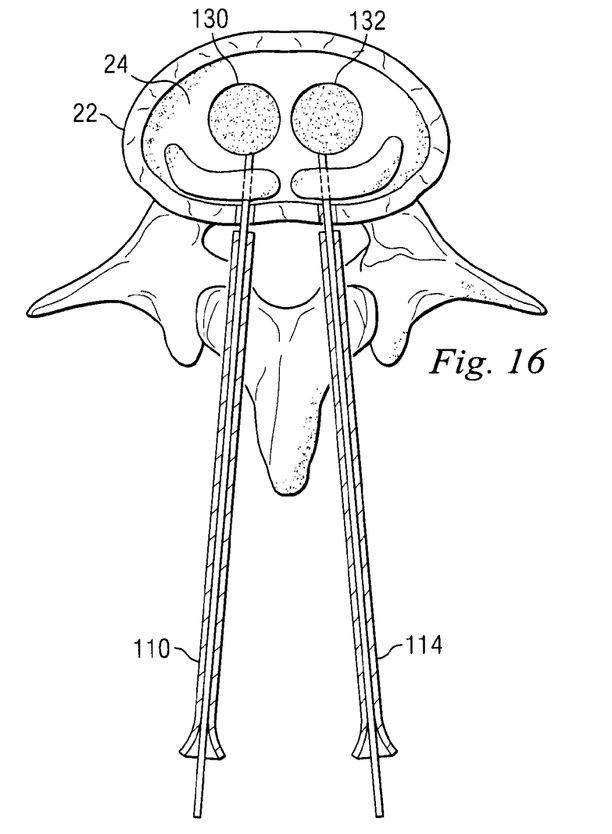
FIGS. 16-17 are sequence views of an intervertebral disc treatment according to another embodiment of the present disclosure.
Figure 17:
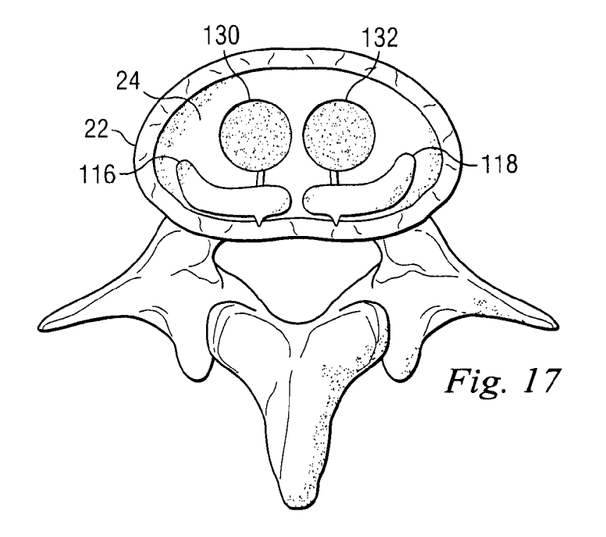

Referring now to FIGS. 16-17, in this embodiment, a substantially similar method of nucleus augmentation as the procedure described above for FIGS. 14-15 may be performed. In this embodiment, however, as described in FIGS. 8-9, spacing portions 130, 132 for creating the more centralized nucleus spaces may be detached to remain in the nucleus tissue as implants.

Although the instruments and implants described are suitable for intervertebral applications, it is understood that the same implants and instruments may be modified for use in other regions including an interspinous region or a bone cavity. Furthermore, the instruments and implants of this disclosure may be incorporated in certain aspects into an intervertebral prosthesis device such as a motion preserving artificial disc.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method for treating a nucleus pulposus of an intervertebral disc, the method comprising:
   creating a first opening to access the intervertebral disc;
   creating a second opening to access the intervertebral disc;
   inserting a first space creation instrument having a first spacing device through the first opening and into the nucleus pulposus of the intervertebral disc;
   inserting a second space creation instrument having a second spacing device through the second opening to access the intervertebral disc;
   inserting a third spacing device into the nucleus pulposus of the intervertebral disc and expanding the third spacing device with a third biomaterial;
   injecting a first biomaterial into the first spacing device to expand the first spacing device;
   injecting a second biomaterial into the second spacing device to expand the second spacing device;
   wherein the first spacing device conforms to an annulus of the intervertebral disc;
   wherein the third spacing device is inserted through the first spacing device; and
   wherein the expansion of the first and second spacing devices occur without removing a portion of the nucleus pulposus.

2. The method of claim 1 wherein the first opening is in an annulus of the intervertebral disc.

3. The method of claim 1 further comprising detaching the first spacing device from the first space creation instrument.

4. The method of claim 1 wherein the first biomaterial is the same as the second biomaterial.

5. The method of claim 1 wherein at least one of the first or second biomaterials is curable in situ.

6. The method of claim 1 further comprising inserting a material delivery instrument through the first spacing device and injecting a third biomaterial into the nucleus pulposus.

* * * * *